United States Patent
Mooney et al.

(10) Patent No.: US 10,226,361 B2
(45) Date of Patent: Mar. 12, 2019

(54) QUASI PASSIVE ASSISTIVE DEVICE

(71) Applicant: REHABILITATION INSTITUTE OF CHICAGO, Chicago, IL (US)

(72) Inventors: Luke M. Mooney, Westford, MA (US); Elliott J. Rouse, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 15/247,531

(22) Filed: Aug. 25, 2016

(65) Prior Publication Data

US 2017/0056209 A1 Mar. 2, 2017

Related U.S. Application Data

(60) Provisional application No. 62/209,748, filed on Aug. 25, 2015.

(51) Int. Cl.
| | |
|---|---|
| *A61F 2/66* | (2006.01) |
| *A61F 2/68* | (2006.01) |
| *A61F 2/50* | (2006.01) |
| *A61F 2/74* | (2006.01) |

(52) U.S. Cl.
CPC ............ *A61F 2/6607* (2013.01); *A61F 2/68* (2013.01); *A61F 2002/5006* (2013.01); *A61F 2002/5079* (2013.01); *A61F 2002/6657* (2013.01); *A61F 2002/747* (2013.01); *A61F 2002/748* (2013.01)

(58) Field of Classification Search
CPC .. A61F 2/66; A61F 2/6607; A61F 2002/6657; A61F 2002/6854; A61F 2002/701
See application file for complete search history.

(56) References Cited

U.S. PATENT DOCUMENTS

| | | | | |
|---|---|---|---|---|
| 2014/0088730 A1* | 3/2014 | Hansen | ............... | A61F 2/6607 623/52 |
| 2015/0202057 A1* | 7/2015 | Zahedi | .................. | A61F 2/64 623/26 |
| 2017/0042703 A1* | 2/2017 | Pusch | .................. | A61F 2/66 |

* cited by examiner

*Primary Examiner* — Bruce E Snow
(74) *Attorney, Agent, or Firm* — Drinker Biddle & Reath LLP (57) ABSTRACT

Implementations of a quasi-passive assistive device are disclosed. Such a device may comprise a spring mechanism that increases stiffness similar to a biological ankle. In one implementation, the spring mechanism may comprise a piston, valve, springs, or other elements to match a biological stiffness profile similar to that of a biological ankle. In one implementation, an apparatus for an artificial ankle is disclosed, comprising a piston coupled to a spring and the piston connected to a valve. The spring and the piston may store energy during dorsiflexion of the ankle and the spring and the piston release energy during plantarflexion of the ankle. The piston may store and release energy through the use of the valve.

9 Claims, 7 Drawing Sheets

QUASI PASSIVE ASSISTIVE DEVICE

CROSS-REFERENCE TO RELATED APPLICATIONS

This application claims the priority benefit of U.S. Provisional Application No. 62/209,748, filed Aug. 25, 2015 and incorporated herein by reference in its entirety.

FEDERALLY SPONSORED RESEARCH OR DEVELOPMENT

This invention was made with Government support under Grant No. W81XWH-09-2-0143 awarded by the U.S. Army Medical Research and Material Command. The Government has certain rights in the invention.

TECHNICAL FIELD

This disclosure relates generally to mobility assistive devices and, more particularly, to a quasi-passive assistive device.

BACKGROUND

The mobility of transtibial, or below knee, amputees is limited by the design of common, passive ankle-foot prostheses. The muscles that span the biological ankle joint provide the majority of mechanical power during walking. Consequently, the loss of this joint causes these individuals to walk up to 40% slower and expend at least 20% more metabolic energy, when compared to non-amputees; a metabolic burden typically associated with carrying 15 kg.

Historically, energy storage and release (ESR) prosthetic feet have been developed to reduce some of the aforementioned deficits associated with transtibial amputations. These prosthetic feet typically consist of an anthropomorphic carbon fiber leaf spring, where the leaf spring is cantilevered from the heel anteriorly towards the toe. The purpose of the leaf spring is to store elastic energy as the foot is dorsiflexed during the stance phase of walking, the region of the gait cycle when weight is borne by the leg. Ideally, this energy is returned to the wearer at terminal stance phase, when the ankle plantarflexes to propel the wearer forward.

As a result of the cantilever nature of the leaf spring in the design of ESR prosthetic feet, they do not provide the biologically appropriate torque-angle and stiffness properties during walking. That is, as the center of pressure moves anteriorly during stance phase, the stiffness of the cantilever leaf spring decreases exponentially. This opposes the trend known to occur in the biological ankle joint. The stiffness of the biological ankle joint is known to increase linearly during the dorsiflexion region of stance phase. Therefore, the anthropomorphic cantilever design of ESR feet results in non-biological mechanical behavior, likely contributing to the gait deficits of transtibial amputees.

Researchers have previously designed novel passive and quasi-passive prosthetic feet to address the limitations of current technology. Hansen and Nickel designed an ankle-foot prosthesis to increase balance during walking and standing. To this end, their device incorporated a locking mechanism to transition between two stiffness modes to provide the appropriate kinematic rollover shape observed during walking and standing. Additionally, Collins and Kuo developed a quasi-passive ankle prosthesis that recycles the impact energy from heel contact and returns it during push off. This prosthesis technology was shown to increase ankle push off work and decrease the metabolic energy consumed during walking, when compared to walking with a conventional prostheses. Lastly, recently developed powered ankle prostheses have been shown to normalize transtibial amputee gait characteristics.

Previous work in the development of novel ankle-foot prostheses is encouraging and underscores the importance of prosthesis stiffness properties, as well as the significance of energy returned to the wearer during locomotion. Unfortunately the clinical impact of such work has been limited by mechanical complexity; non-biological, cantilever stiffness behavior; as well as substantial mass.

By design, commonly worn energy storage and release (ESR) prosthetic feet cannot provide biologically realistic ankle joint torque and angle profiles during walking. Additionally, their anthropomorphic, cantilever architecture causes their mechanical stiffness to decrease throughout the stance phase of walking, opposing the known trend of the biological ankle.

BRIEF SUMMARY

Embodiments of a quasi-passive assistive device are disclosed. Such a device may comprise a spring mechanism that increases stiffness similar to a biological ankle. In an embodiment, the spring mechanism may comprise a piston, valve, springs, or other elements to match a biological stiffness profile similar to that of a biological ankle.

In an embodiment, an apparatus for an artificial ankle is disclosed, comprising a piston coupled to a spring and the piston connected to a valve. The spring and the piston store energy during dorsiflexion of the ankle and the spring and the piston release energy during plantarflexion of the ankle. The piston stores and releases energy through the use of the valve.

DETAILED DESCRIPTION

In different embodiments, a quasi-passive pneumatic ankle-foot prosthesis is detailed that is able to replicate the biological ankle's torque and angle profiles during walking. Quasi-passive refers to a device that uses a small amount of energy, typically electrical energy to power a microcontroller, but does not provide any net-positive mechanical energy. The prosthetic ankle may be comprised of a pneumatic piston, bending spring and solenoid valve. The mechanical properties of the pneumatic ankle prosthesis may be characterized using a materials testing machine and the properties are compared to those from a common, passive ESR prosthetic foot. The characterization can span a range of ankle equilibrium pressures and testing locations beneath the foot, analogous to the location of center of pressure within the stance phase of walking. Embodiments of a pneumatic ankle prosthesis can provide biologically appropriate trends and magnitudes of torque, angle and stiffness behavior, when compared to the passive ESR prosthetic foot. Embodiments may comprise a control system for the quasi-passive device and clinical testing of the pneumatic ankle to demonstrate efficacy.

Figure 8:
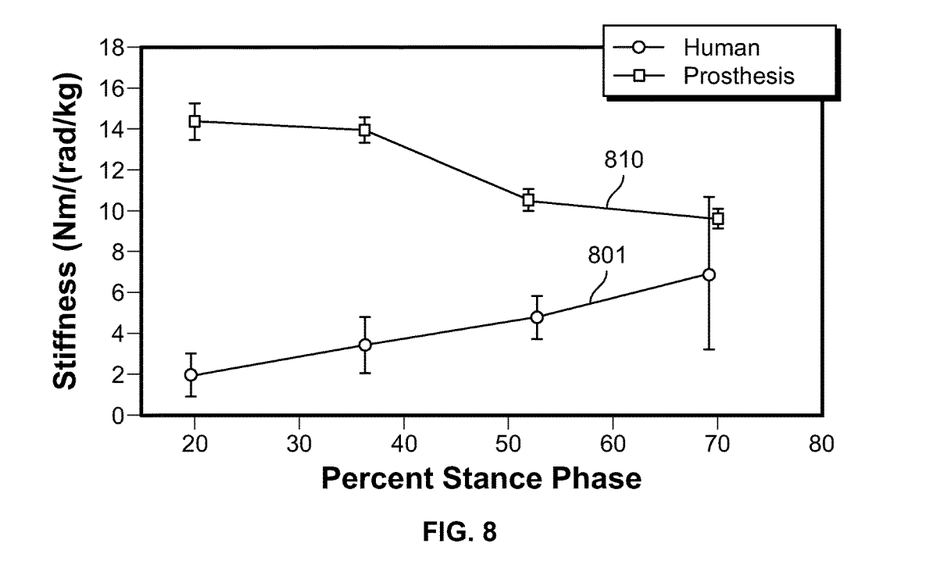
FIG. 8 depicts a plot of stiffness for a human ankle against a plot of stiffness for a prior art prosthesis.

In an embodiment, the design of an ankle-foot prosthesis is disclosed that may replicate the biological ankle's natural stiffness behavior. For example, curve 801 in FIG. 8 shows a biological ankle's natural stiffness behavior. In an embodiment, a customizable, lightweight and simple design may reduce the locomotory deficits of transtibial amputation. Embodiments may be designed to provide biomimetic torque-angle behavior, independent of center of pressure location. An embodiment using a materials testing machine and the results are compared to the mechanical properties of a common ESR prosthetic foot.

Mechanism Architecture. In this section, the design of an embodiment of a pneumatic quasi-passive ankle-foot prosthesis mechanism, prosthesis 100, is detailed. Various design objectives include developing a customizable, lightweight ankle prosthesis mechanism that replicated the stiffness characteristics shown recently for the biological ankle joint during walking. To this end, FIG. 1A displays a prosthesis 100 comprising pneumatic piston 110 that may be used in series with a spring 130. The prosthesis 100 may provide a modulated equilibrium position, where equilibrium position refers to the angular position that causes zero torque.

Figure 1A:
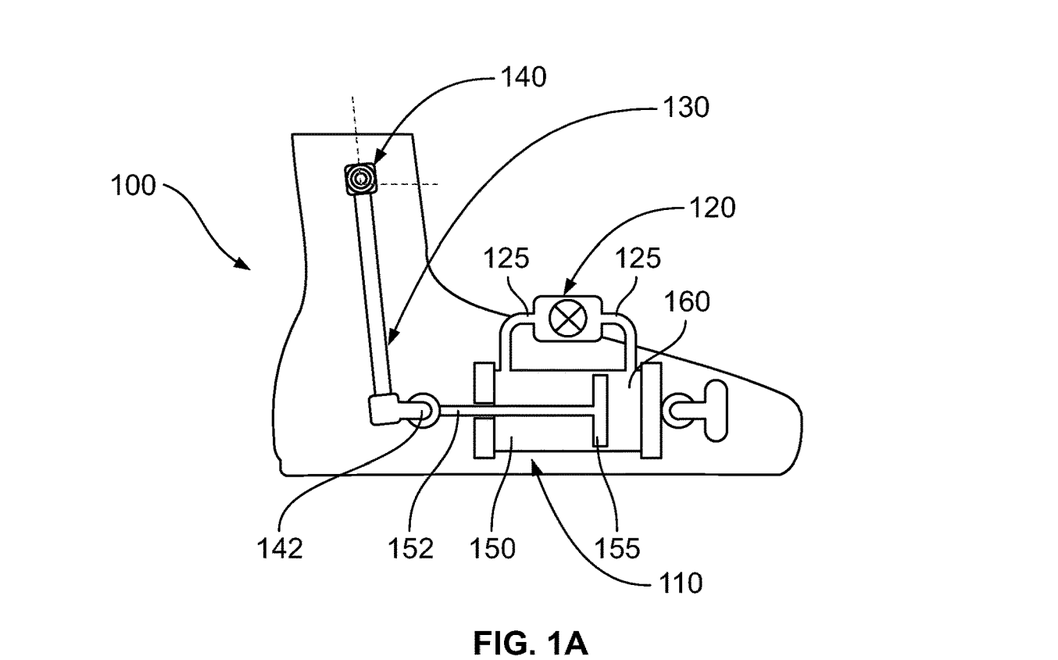
FIG. 1A depicts a side view of an embodiment of an ankle device.

A piston head 155 coupled to a connecting rod 152 is inserted into an opening of a side of the piston 110. The connecting rod 152 may be coupled to the spring 130 with fastener 142. The piston head 155 separates the piston 110 into a compression chamber 150 and a vacuum chamber 160. Air flow between the compression chamber 150 and the vacuum chamber 160 may be controlled with a miniature electric solenoid valve 120. The solenoid valve 120 connects to the piston 110 through tubes 125.

Using a mechanical bending spring for spring 130 preferably results in a prosthesis with less mass than one in which heavier components, such as coil springs, may be used, although coil springs or other suitable springs, such as leaf springs or torsion springs, could be used instead of a mechanical bending spring. A mechanical bending spring may be made of fiberglass or another appropriate material, such as metal, carbon fiber, rubber, etc.

Figure 1B:
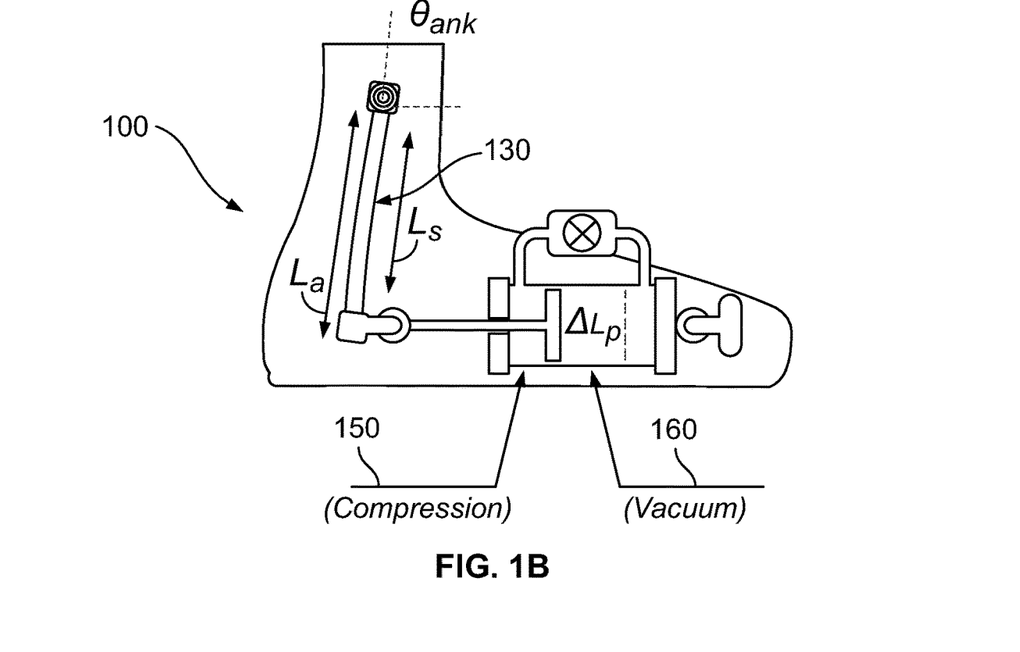
FIG. 1B depicts another side view of the ankle device.

During operation, the torque-angle relationship of the prosthesis 100 is governed by the force through the pneumatic piston 110 and lever arm of the bending spring 130. FIG. 1B shows the prosthesis 100 with relevant variables shown and defined below. As the ankle is dorsiflexed, the total piston length is elongated and pressure increases in the compression chamber 150. When the solenoid valve 120 is opened, the pressure between compression chamber 150 and the vacuum chamber 160 is equalized, and the prosthesis 100 rotates freely around the joint. Upon heel contact, the foot is plantarflexed and the solenoid valve 120 is closed. As the foot dorsiflexes, energy is stored in the change in gas volumes between the compression chamber 150 and the vacuum chamber 160, as well as in the flexing of the bending spring 130. The energy stored in the piston and the bending spring 130 is released, as the ankle of the prosthesis 100 travels back through its range of motion at "push off," which is the position when the toe of the prosthesis pushes against the ground to lift the prosthesis 100 off the ground and begins a swing phase of the limb to which the prosthesis 100 may be attached.

To obtain an expression for the torque-angle relationship of the prosthesis 100, the gas dynamics may be modeled. Assuming negligible transfer of heat between the piston 110 and the surroundings (i.e. adiabatic process), the pressures before and after the adiabatic process are governed by equation 1

$$P_A V_A^\gamma = P_B V_B^\gamma$$

where P and V denote absolute pressure and volume; subscripts A and B denote after and before the adiabatic process, and $\gamma$ is a constant, known to be 7/5 for diatomic gasses most commonly found in air. The equation for piston force, equation 1 is considered for both the compression and vacuum sides of the piston 110 including area consumed by the piston shaft, equation 2, $$F = P_{ambs} a_s + \frac{(a - a_s) P_{B1} V_{B1}^\gamma}{(V_{B1} - (a - a_s) \Delta L_p)^\gamma} - \frac{a P_{B2} V_{B2}^\gamma}{(V_{B2} + a \Delta L_p)^\gamma}$$

where $P_{amb}$ is the ambient pressure, $a_s$ is the cross-sectional area of the piston shaft, a is the cross-sectional area of the piston bore, $\Delta L_p$ is the change in piston length (stroke), and subscripts 1 and 2 denote the compression and vacuum sides of the piston, respectively. The torque about the ankle, $\tau$, can be determined by equation 3

$$\tau = F L_a \cos(\theta_{ank})$$

where $L_a$ is the length of the total moment arm.

To obtain a corresponding expression for ankle angle, the contribution from the change in piston length may be considered with the contribution from the flexing of the bending spring 130, equation 4, $$\theta_{ank} = \theta_B + \Delta\theta_p + \Delta\theta_s$$

where $\Delta\theta_p$ is angular contribution from the change in piston length, $\Delta\theta_s$ is the angular contribution from the flexing of the bending spring and $\theta_B$ is the angle before the process (before ankle dorsiflexion). Using the small angle approximation and the equation governing bending spring displacement the following equations were defined in equation 5

$$\Delta\theta_p = \frac{\Delta L_p}{L_a}$$

and equation 6

$$\Delta\theta_s = \frac{F L_s^3}{L_a 3 EI}$$

where $L_s$ is the length of the bending spring 130, E is the elastic modulus of the bending spring 130, and I is the cross-sectional moment of inertia of the bending spring 130.

The overarching equation that governs the mechanical properties of the prosthesis 100, torque as a function of angle, can be calculated numerically. By substituting equations 5 and 6 into equation 4 and solving for $\Delta L_p$, then substituting into equation 2, the piston force, F, can be used to determine ankle torque with equation 3. These equations cannot be solved in closed form, and must be solved numerically or through the use of an intermediate variable.

By inspection of equation 2, the stiffness characteristics of the ankle of the prosthesis 100 can be tuned by increasing or decreasing the equilibrium pressure within the piston system, $P_B$. This highlights the customizable nature of embodiments of the prosthesis 100.

Mechanical Design. The prosthesis 100, as shown in the embodiment in the figures, can provide biomechanically appropriate ankle walking kinetics and kinematics in an anthropomorphic envelope. The prosthesis 100 may be designed to meet the requirements of a 70 kg person walking at self-selected speeds, while fitting in the biological form factor of a $1^{st}$ percentile male. These biomechanical requirements were determined from the weight-normalized kinematics and kinetics from a reference dataset. It was assumed that the prosthesis 100 would account for 30% of the volume and mass between the knee and ankle joints, and the entire volume and mass of the foot, accounting for approximately 2.6% of total body mass. The resulting specifications are shown in Table 1. These requirements provided the foundation for the mechanical design of the prosthesis 100.

TABLE 1

Prosthesis Design Specifications

| Parameter | Value |
| --- | --- |
| Range of motion | 0.4 radians |
| Max torque | 80 Nm |
| Mass | <1100 g |
| Height | <178 mm |
| Foot length | <232 mm |

The architecture of the pneumatic ankle prosthesis embodiment was designed to handle the loads and torques of level ground walking, while minimizing mass and length in a biological form factor.

Figure 2:
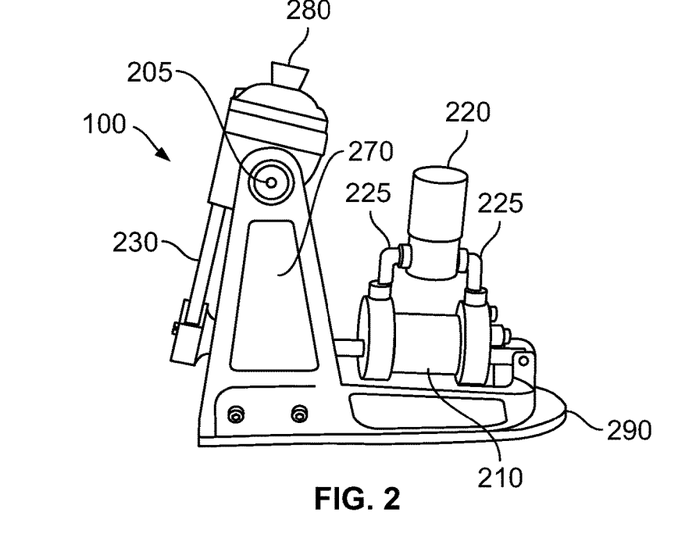
FIG. 2 depicts another side view of the ankle device.

FIG. 2 displays an embodiment of a prosthesis 200 according to the general principals shown by the representation of the prosthesis 100 in FIG. 1. The pneumatic cylinder 210 forms the outer portion of the piston, and may be of model PSD3 (Fabco-Air, Inc., Gainesville, Fla.), with a bore diameter of 27 mm, a stroke length of 38 mm, and a maximum rated pressure of 1.4 Mpa and a resulting in a maximum output force of 800 N (model: PSD3, Fabco-Air, Inc., Gainesville, Fla.).

The solenoid 220 may be model A2015-C203 (Gems Sensors & Controls, Plainville, Conn.). In an embodiment, the spring 230 may be 65 mm long ($L_s$), 27 mm wide, 6 mm thick in the bending direction, and made from a unidirectional fiberglass composite (model: GC-67-UB, Gordon Composites, Montrose, Colo.). The spring 230 may be integrated into a 100 mm ($L_a$) moment arm that links the pneumatic piston to the ankle joint. The moment arm length selection is a tradeoff between the cylinder bore, length and force with the vertical height of the ankle's center of rotation, which may be chosen to fit preferred design criteria. The vertical height of the center of rotation 205 may be 130 mm. (This patent refers to dorsiflexion and plantarflexion, and flexion may occur at the center of rotation 205.) The cylinder stroke length and moment arm can result in a 0.36 radian unloaded range of motion, with an additional 0.1 radians of dorsiflexion achieved through loading of the bending spring. The moment arm length and maximum cylinder force resulted in a maximum ankle torque of 80 Nm, which is approximately 400% that typically borne by ESR prosthetic feet and 70% of the maximum torque exerted by the biological ankle of a 70 kg individual.

An aluminum proximal pyramid mount 280 constrained one end of the bending spring 230 and rotated on two angular bearings, each with a load rating of over 1300 N (model: Kit8330, NationSkander California Corporation, Anaheim, Calif.). The foot 290 may be comprised a lightweight plastic sole and a rigid aluminum housing 270 that prevented structural bending of the foot 290. The mechanical components of the ankle embodiment, depicted in FIG. 2, have a total mass of 1040 g, a height of 177 mm, and a foot length of 188 mm, all within the design specifications for a $1^{st}$ percentile male.

It should be understood from the teachings disclosed in this patent that many possible configurations of springs and air cylinders could be used to develop a prosthesis that approximately matches the shape of the torque-angle curve (which is stiffening) produced by a human ankle. For instance, the positions of the piston and the spring could be reversed, or the piston could be in any relative order with respect to other springs. As another example, in other embodiments, the piston does not require an opening and closing valve.

Figure 10A:
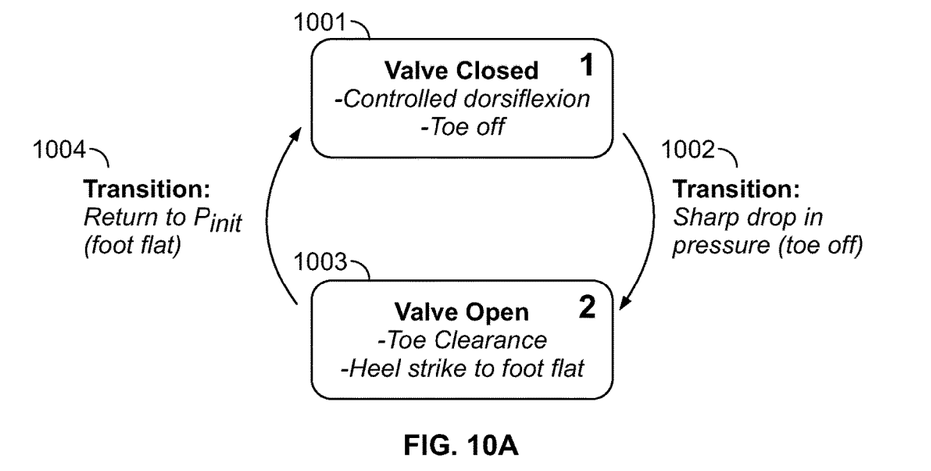
FIG. 10A depicts a representation of an exemplary control system to open and close valves associated with an embodiment of a prosthesis.

A prosthesis may be controlled using a control system. The pneumatic prosthesis is capable of behaving in two separate modes in order to best accommodate the user: a free-swinging mode when the valve is open, and a high-stiffness mode during stance phase when the valve is closed. In order to allow the prosthesis to behave in the appropriate manner, the valve must open and close at the correct time. When the solenoid valve is open, air is able to flow freely from one side of the cylinder to the other and the prosthesis is able to rotate about the ankle axis. Conversely, when the valve is closed, air is unable to pass from one side of the cylinder to the other, and thus stores energy as the foot dorsiflexes and returns energy when the user pushes off. By design, the solenoid valve is intended to be closed at the initiation of foot flat until the user has fully pushed off. The valve then opens, allowing the prosthesis to rotate freely. Since the cross sectional area on side 2 of the cylinder is larger and both sides have equal pressure, there will be a greater force on side 2 of the cylinder. As a result, the ankle will always have a tendency to dorsiflex when the valve is opened, which aids in toe clearance during swing phase. Finally, the valve will remain open during heel-strike, allowing the ankle to naturally plantarflex, and will close once foot-flat occurs. FIG. 10A displays a schematic of an exemplary control system with description and transition events described. Step 1001 shows the valve close during stance phase, from controlled dorsiflexion to toe off. Step 1002 reflects a transition phase, for instance upon a sharp drop in pressure applied to the prosthesis from the ground, which would reflect a "toe off" event (where the toe of the prosthesis lifts off the ground). Step 1003 reflects the valve opened during swing phase, from toe clearance (shortly after toe off), through the heel of the prosthesis striking, to "foot flat" (when the sole of the prosthesis is flat on the ground).

Step 1004 reflects a second transition phase, for instance upon a return to pressure to the prosthesis applied from the ground, which would reflect a "foot flat" event, causing a return to Step 1001 (valve closed).

Figure 10B:
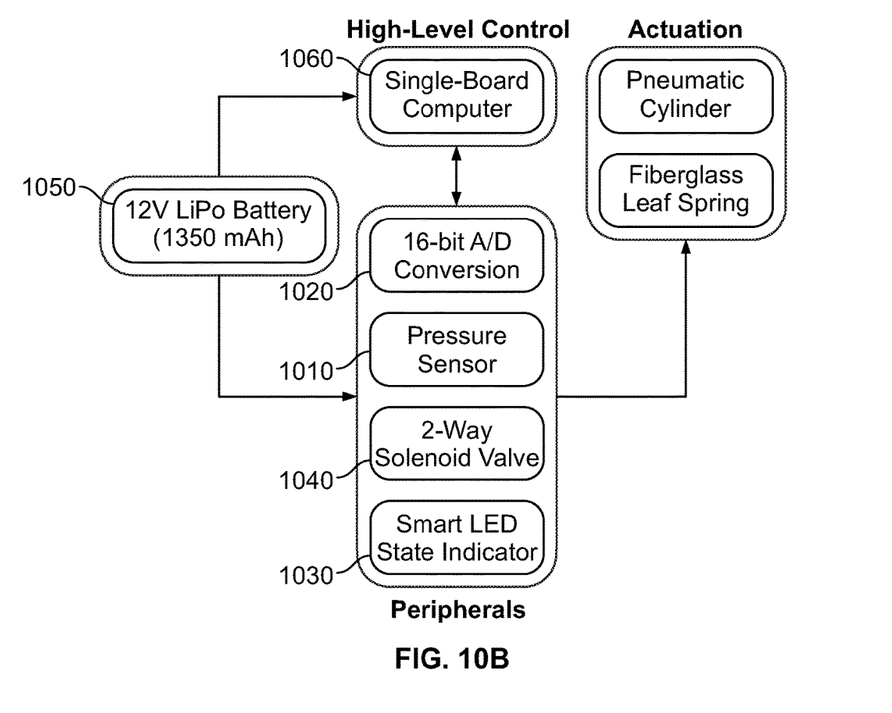
FIG. 10B depicts a representation of exemplary hardware used to open and close valves associated with an embodiment of a prosthesis.

A finite-state machine may be implemented on a single-board computer (Model B, Raspberry Pi Foundation, Cambridgeshire, UK) in addition to a variety of peripheral hardware (shown in FIG. 10B). A pressure sensor 1010 (SSCDLNN100PGAA5, Honeywell, Morristown, N.J.) may be used in combination with a 16-bit analog-to-digital converter 1020 (ADS1115, Texas Instruments, Dallas, Tex.) to monitor the pressure on the compression side of the piston 200. An LED 1030 (MinM, ThingM Corp., San Francisco, Calif.) may be used in order to indicate which state the prosthesis 200 is in (open vs. closed), and a circuit containing a MOSFET (STU60N3LH5, STMicroelectronics, Geneva, CH) was used as a switch for opening and closing the solenoid valve 1040. A three-cell 12V lithium polymer battery 1050 may be used to provide power to the single-board computer 1060 and the solenoid valve, making the system mobile.

State determination may be based on the readings that were continuously collected from the pressure sensor at 800 Hz. Proper opening of the valve 1040 was obtained by the observance of a large pressure drop (Pdrop) between consecutive readings from the pressure sensor 1010 (P, Pprev). A threshold (Pthreshold) was included in this condition in order to prevent the valve 1040 from opening while the user was not in walking mode (e.g. shuffling feet, turning around, or shifting weight while standing). To close the valve 1040 at the appropriate time, the dynamics of the pressure inside the cylinder on the compression side may be measured. While the valve 1040 is open, the pressure is identical on both the compression side and the vacuum side of the piston. When the ankle is fully dorsiflexed, the volume in the cylinder is larger compared to when the ankle is plantarflexed. As a result, the pressure will rise as the ankle plantarflexes during heel-strike to foot-flat. This allows the position of the ankle of the prosthesis 200 to be determined by the pressure while the valve is open. Since the ankle is initially set up in the ideal position and at the pressure found from the optimization (Pinit), the valve 1040 should close once the pressure returns to that original pressure in preparation for the next gait cycle. An upper and lower limit (PB, PS) was utilized to allow for the valve 1040 to close once the pressure, P, returned to within a range of the initial pressure.

After the system senses the transition from Step 1001 to Step 1003 (FIG. 10A), there is a delay which allows the pressure to return to its initial pressure. This condition allows the user to fully push off and capture all of the energy that was stored during dorsiflexion. In other words, the prosthesis may behave in two distinct modes. While the valve is open, the ankle of the prosthesis is free to rotate, and allows the user to experience a biomimetic heel-strike to foot-flat. It also gives the added benefit of dorsiflexing immediately after toe-off when the valve is opened in order to aid in toe clearance. While the valve is closed during stance phase, the foot stores and returns energy appropriately during the stance phase of walking. The control of the solenoid valve behaves similarly to a clutch.

Other embodiments may incorporate a mechanism to increase stiffness while the user of the prosthesis is standing, which may assist with the clinical viability of the prosthesis.

Methods

To obtain an understanding of how the mechanical properties of the pneumatic ankle prosthesis 200 compare to common commercially available, prior art ESR prosthetic feet, both were characterized in a materials testing machine.

Testing of the Pneumatic Prosthesis. The prosthesis 200 was secured to an aluminum testing rig that was fastened to the high-capacity frame of the testing machine (model: 1125 with A30-33 load cell, Instron, Norwood, Mass.). The testing machine was chosen for its ability to apply precise displacements while synchronously measuring resultant forces. The starting angle of the pneumatic ankle of the prosthesis 200 was set to maximum plantarflexion (0.2 radians, mechanically adjustable) to characterize the full dorsiflexion range of motion. During testing, a servo-ram was lowered, applying a displacement to the pneumatic foot through a high force roller (32 mm radius) mounted to the end of the ram. The roller was used to eliminate sliding friction at the contact between the servo-ram and the foot as the ram traveled linearly. The perpendicular distance of the ram to the center of rotation of the ankle was varied, analogous to differing centers of pressure (COP) distances beneath the foot. The ankle was characterized at ram distances of 102 mm, 122 mm, 145 mm, 168 mm and 185 mm from the center of rotation anteriorly. These distances were chosen because they span the testable range of the foot, accounting for translation (rolling) of the ram along the anterior-posterior axis of the foot as the ram lowered and the ankle dorsiflexed. Two equilibrium pressures were tested at each ram distance, 310 kPa and 413 kPa. At the ram distance of 145 mm, five equilibrium piston pressures were tested, 0 kPa, 103 kPa, 206 kPa, 310 kPa and 413 kPa (gauge pressure). A single trial was acquired at each ram distance and equilibrium pressure, with force data acquired at 10 Hz. During testing, the ram lowered with a velocity of 20 mm/min and the test was terminated when the torque about the ankle reached approximately 70-80 Nm.

Testing of the Commercial ESR Prosthesis. An identical protocol was used to test the ESR prosthetic foot (model: Seattle Low Profile, 27 cm, category 3; Trulife, Poulsbo, Wash.). The footshell was removed from the foot prior to testing. This was to eliminate substantial local compression of the foam footshell not likely to be experienced during locomotion. The foot was secured to the testing rig at a neutral angle (0 radians) and the servo-ram applied a displacement to the foot and recorded the force. Five ram distances were tested spanning the length of the foot; the ankle was characterized at ram distances of 53 mm, 73 mm 109 mm 129 mm and 154 mm from the ankle's center of rotation. Since the ESR has a fixed ankle (no mechanical revolute joint), an axis was determined to be the ankle's center of rotation and was consistently used in the analysis.

Data Analysis. The force and displacement measurements were converted to ankle torque, $\tau$, and angle, $\theta_{ank}$, using the geometry of the measurement setup and prosthetic feet. All data was low-pass filtered using a bi-directional third order Butterworth filter with a cutoff frequency of 5 Hz. For the prosthesis 200, MATLAB (The Mathworks, Natick, Mass.) was used to calculate the stiffness, $d\tau/d\sigma_{ank}$. A second order polynomial was fit to four points surrounding each point, and the polynomial coefficient was used to quantify the derivative. For the ESR prosthetic foot, linear regression was used to estimate the stiffness because the stiffness did not vary with angle. All data are reported as mean±standard deviation. Data analysis was performed on a computing device with memory and a microprocessor.

Results

Figure 3:
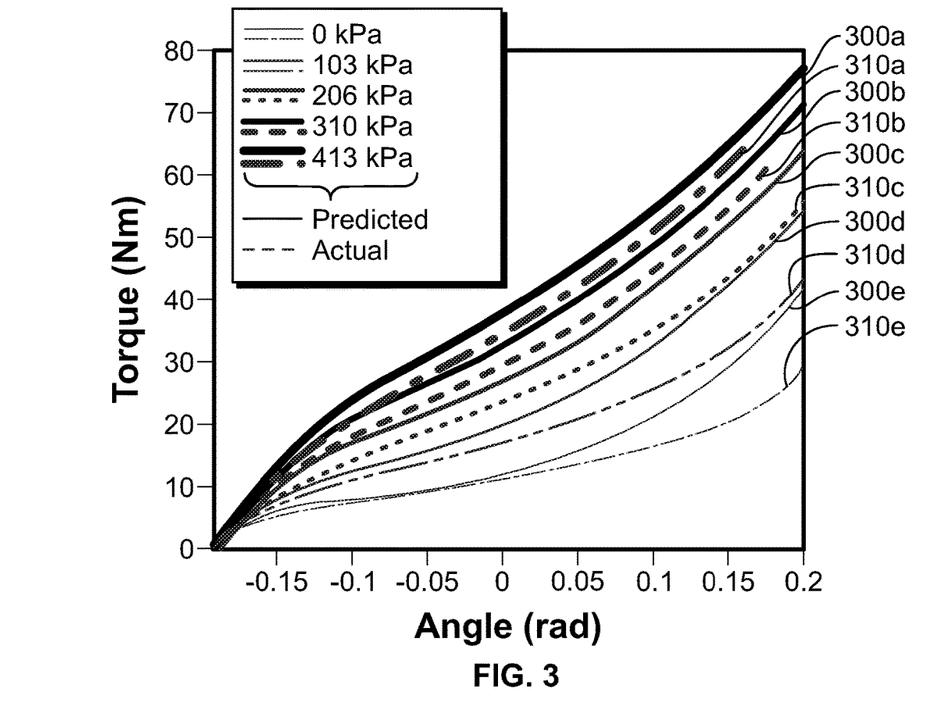
FIG. 3 depicts a graph of certain torque values.

Mechanical Behavior and Equilibrium Pressure. The prosthesis 200 was tested at five equilibrium pressures, ranging from 0 kPa to 413 kPa at a ram distance of 145 mm. As the pressure was increased, the torque increased as a function of angle. FIG. 3 displays curves of actual and model predicted values of torque as a function of angle for the prosthesis 200. Curve lines 300a-300e represent predicted data at the corresponding equilibrium gauge pressures displayed in FIG. 3. Curve lines 310a-310e represent actual data at the corresponding equilibrium gauge pressures displayed in FIG. 3. The color denotes equilibrium gauge pressure and the dash/solid represents actual or predicted data. Note the model agreement increases with pressure. This is likely a result of the simplified bending spring modeling and adiabatic assumption. The torque varied from 0 Nm to approximately 30 Nm-80 Nm, depending on the equilibrium pressure tested. The equations describing the prosthesis 200 used to predict the torque as a function of angle. The model predicted data are shown for comparison for the same equilibrium pressures. The trends in the data generally agree, with greater deviation at low equilibrium pressures and dorsiflexed ankle angles. At 0.1 radians dorsiflexion, the mean difference in torque was 5.8±1.2 Nm, when compared across equilibrium pressures.

Figure 4A:
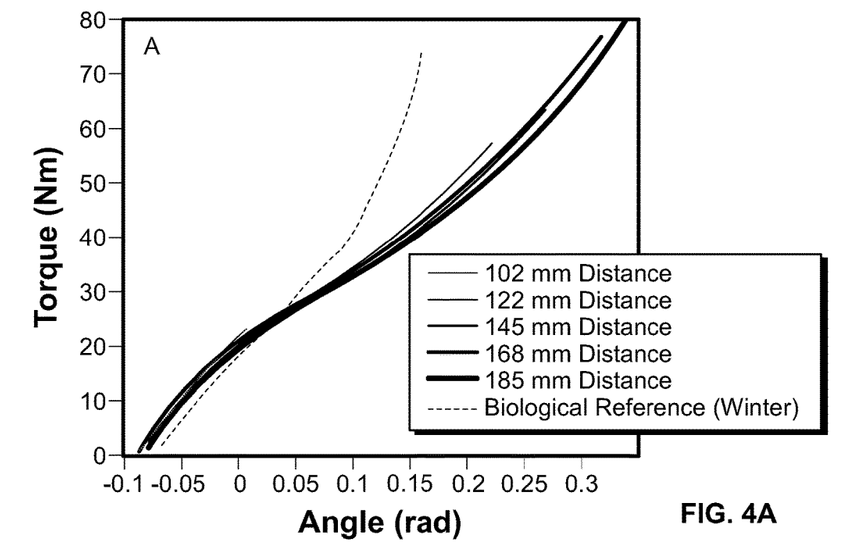
FIG. 4A depicts another graph of certain torque values.
Figure 4B:
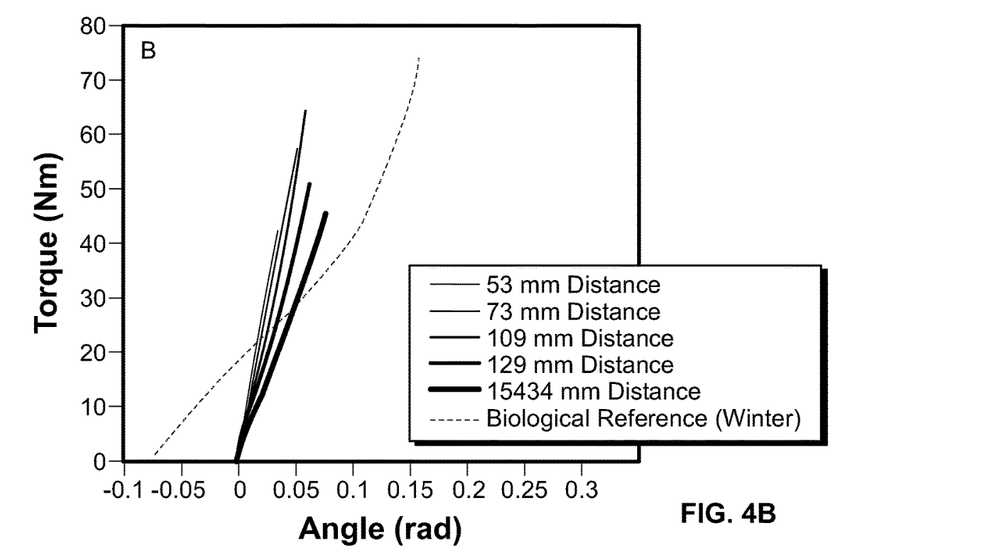
FIG. 4B depicts another graph of certain torque values.

Mechanical Behavior and Ram Distance. FIG. 4A displays a graph indicating torque as a function of angle for the prosthesis 200 (413 kPa), shown with biological reference data. Note the five distances tested agree in the torque-angle space, a result of the articulated mechanical design. This relationship can be adjusted by varying the equilibrium pressure in the cylinder of the piston of the prosthesis, such as prosthesis 200. FIG. 4B displays a graph indicating torque as a function of angle for the ESR prosthetic foot, shown for the biological reference. Note that the stiffness of the ESR foot decreases with increasing distance tested. The torque and angle behavior were quantified at several ram distances for both the pneumatic ankle prosthesis and the ESR ankle prosthesis. The torque-angle relationship of the prosthesis 200 did not vary with ram distance, shown at an equilibrium pressure of 413 kPa (FIG. 4A). The torque increased to approximately 45 Nm at 0.15 radians dorsiflexion with a total of approximately 0.3-0.4 radians displacement. Thus, the stiffness of the prosthesis 200 did not vary with ram distance. The torque-angle relationship for the able-bodied ankle is shown for reference.

The torque-angle relationship of the ESR prosthetic foot varied with ram distance (FIG. 4B). As a result, the angular displacement required to generate 40 Nm varied from 0.03-0.06 radians (mean 0.045±0.015 radians), depending on ram distance. As ram distance increased from 53 mm to 154 mm (i.e. the ram was translated anteriorly), the stiffness of the ESR prosthetic foot decreased by 51%. Thus, the stiffness of the ESR foot is a function of the ram distance, analogous to COP location during walking. The stiffness of the ESR prosthetic foot decreases during the stance phase of walking. When compared to the reference dataset for the biological ankle, the stiffness of the ESR is substantially greater severely limiting the magnitude of angular deflection of the ESR prosthetic foot.

Figure 5:
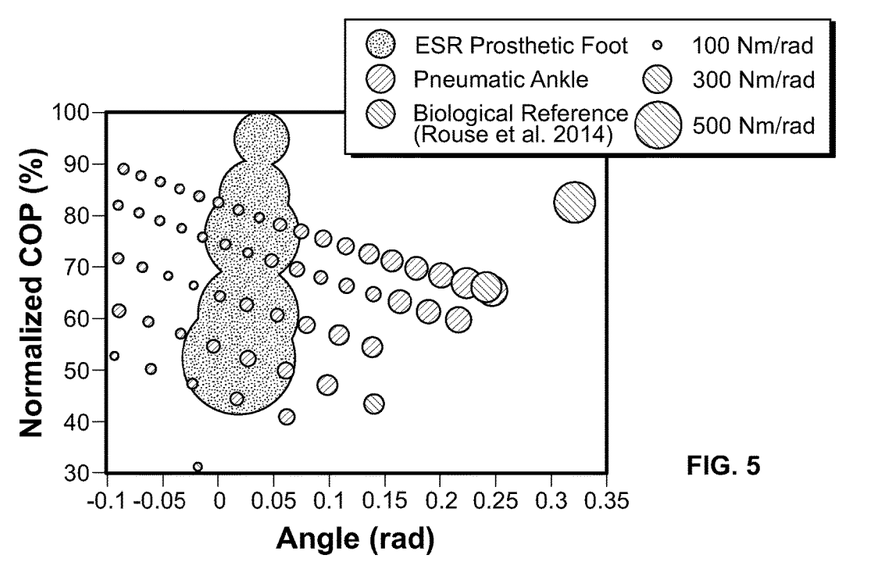
FIG. 5 depicts a plot of certain stiffness values.

Ankle Angle, COP Location and Stiffness. The measured stiffness of the prosthesis 200 was compared to the stiffness of the ESR prosthetic foot, and recently published biological ankle stiffness values. To fully understand how the prosthesis 200 is different than the conventional ESR prosthetic foot, the stiffness data were compared as a function of ankle angle and normalized COP location, as shown in the plot in FIG. 5. The pneumatic ankle prosthesis and the ESR prosthesis had opposing stiffness trends. The pneumatic ankle prosthesis was designed for torque to vary only as function of ankle angle, with stiffness increasing as the ankle is dorsiflexed (FIG. 4A). This design was based on recently published biological data, shown for reference in FIG. 5. FIG. 5 is a display of a plot that reflects stiffness shown as a function of ankle angle and normalized center of pressure (COP). The size of the markers denotes the magnitude of the ankle stiffness at the respective ankle angles and COP location during walking. COP is normalized by foot length, to negate the effect of the different designed lengths of the prosthetic feet. Note that because the stiffness of the pneumatic ankle is only a function of angle, movement along the vertical axis does not affect stiffness magnitude. Corrspondingly, for the ESR foot, stiffness is only a function of COP location, and movment along the horizontal axis does not affect stiffness magnitude.

Normalized COP location was defined as the ram distance divided by the total foot length. The stiffness of the prosthesis 200 (413 kPa) increased by a factor of three, following similar trends to those observed in biological data. Work estimating ankle impedance during walking showed ankle stiffness increasing by a factor of four as the ankle was dorsiflexed and the COP translated anteriorly (COP data obtained from an open dataset). It should be noted that the negative linear trends of pneumatic ankle COP and ankle angle is an artifact of the testing apparatus and protocol.

The behavior of the ESR prosthesis opposed the magnitude and trends of biological stiffness data. The stiffness of the ESR prosthetic foot was at most 11 times greater than the biological ankle, with the stiffness decreasing as ankle angle and center of pressure increased, opposing biological trends.

The error in the model predicted torque-angle relationship of the pneumatic ankle prosthesis decreased with increasing equilibrium pressure, as shown in FIG. 3. This discrepancy may be the result of non-ideal behavior from the bending spring within the mechanism or the idealized adiabatic assumption. The mathematical model of the pneumatic mechanism was used to design the physical specifications, and ideal behavior is not required for use. The error could likely be reduced if the bending spring were characterized, rather than assuming ideal behavior. Furthermore, any discrepancy in tubing volume between the model and the physical system may cause the error displayed in FIG. 3.

The dependence of the pneumatic ankle's mechanical behavior on piston equilibrium pressure presents the opportunity to conveniently customize the pneumatic prosthesis for each individual. The trends of the torque-angle relationship may be modified (FIG. 4A) by increasing or decreasing the equilibrium pressure. Such a convenient and reversible mechanism for mechanical behavior modification presents the possibility for a single prosthesis to provide biologically appropriate mechanical behavior across a range of walking speeds, activity levels and load carriage.

As a result of the cantilever nature of ESR prosthetic feet, their stiffness properties decrease as COP moves anteriorly during the stance phase of walking. To compare stiffness at varying locations of COP and ankle angle, the pneumatic ankle stiffness is approximately constant across the vertical axis (i.e. COP location). Conversely, the stiffness of the ESR prosthesis is approximately constant across the horizontal axis (i.e. ankle angle).

The biologically inspired behavior of the pneumatic ankle prosthesis may be important for earlier release of stored mechanical energy for push off. The increasing stiffness of the pneumatic ankle prosthesis provides the stored energy earlier for the wearer to push off during walking. When stiffness increases as a function of angle, more energy is stored per unit of angular displacement as the ankle is dorsiflexed. Therefore, as the ankle begins plantarflexing during push off, the energy is returned back to the user, with most of the energy stored at the greater angles of dorsiflexion. The motivation for this design is that the earlier return of stored energy may reduce the metabolic energy consumed by the wearer during walking.

The use of the solenoid valve provides the ability to arbitrarily set the equilibrium position of the pneumatic ankle prosthesis. In other words, the solenoid valve may essentially provide the function of a clutch, commonly incorporated in biologically inspired mechanisms. When the solenoid valve is opened, air is free to pass between the piston sides, allowing the joint to rotate freely. Thus, the position at which the solenoid valve is closed becomes the equilibrium position until the valve is opened again. This permits dorsiflexion of the ankle during the swing phase of walking, providing required toe clearance.

Embodiments are shown to have customizable, biologically inspired mechanical properties.

Figure 6:
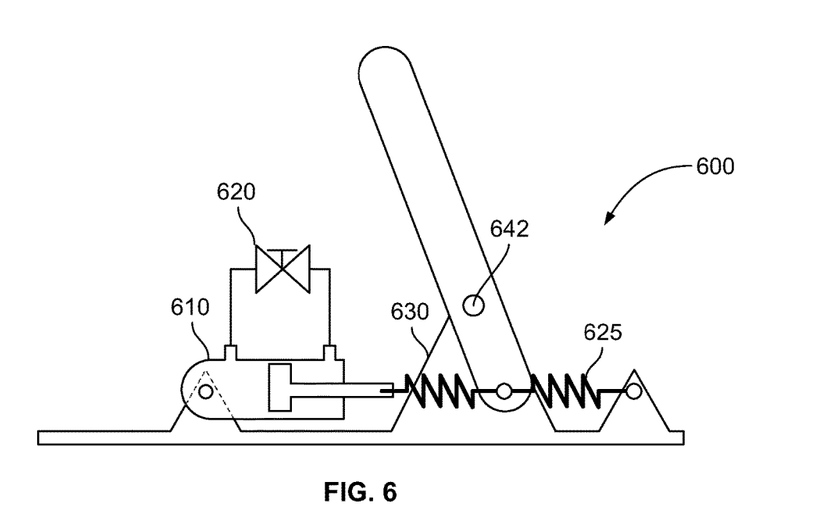
FIG. 6 depicts a side view of an embodiment of an ankle device.

It should be apparent to one of ordinary skill in the art that the teachings in this application directed to a prosthesis could be applied to other devices, such as in one embodiment, a Biomimetic Ankle Stiffness Device (BMASD) 600 is designed to emulate the stiffness of a human ankle during walking. This device can be incorporated into various devices, such as prostheses, orthoses and exoskeletons. The series air cylinder 610 and spring 630 store energy during dorsiflexion and then release that energy during plantar flexion in a biomimetic manner. The BMASD stores and releases energy in a device that mimics a human ankle. The BMASD 600 can uses a double-acting air cylinder in series with stiff spring to store energy in a nonlinear fashion. The air cylinder 610 serves multiple purpose. It acts as an air spring to create the nonlinear stiffness profile, but it also acts as a clutch. The chambers of the air cylinder 610 can be shorted via a valve 620 to bypass the series spring 630 and allow a lighter anti-parallel spring 625 to dorsiflex the BMASD 600 during swing. FIG. 6 depicts one side view of a BMASD 600. The series air spring 630 and linear spring 625 can be optimized to follow a biomimetic stiffness profile. The BMASD may comprise an air cylinder 610 and spring 630 in series that exerts torque about the ankle joint. There is also a soft return spring 625 that dorsiflexes the ankle during swing. The air cylinder 610 is controlled with an air valve 620 that connects the two ports of the air cylinder 610.

Figure 7:
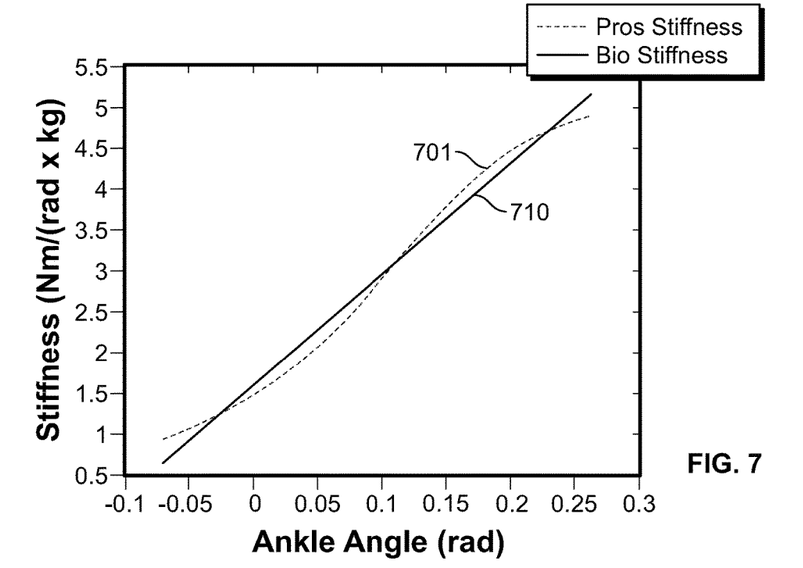
FIG. 7 depicts a plot of certain stiffness values.

The simulated stiffness of the BMASD 600 is shown in FIG. 7. The hardening stiffness of the BMASD 600 is shown in curve 701 and closely follows the observed torque-angle relationship observed during level ground walking shown in curve 700. The ankle stiffness and angle relationship is shown in FIG. 7. The ankle of the BMASD 600 exhibits a linear hardening of stiffness as the ankle of the BMASD 600 dorsiflexes. The BMASD 600 is able replicate this increase in stiffness.

FIG. 8 shows stiffness values of the BMASD 600 normalized by bodyweight for the able-bodied ankle (plot 801) and a conventional, passive prosthesis (plot 810). Note the major differences in stiffness magnitude and trend.

Figure 9A:
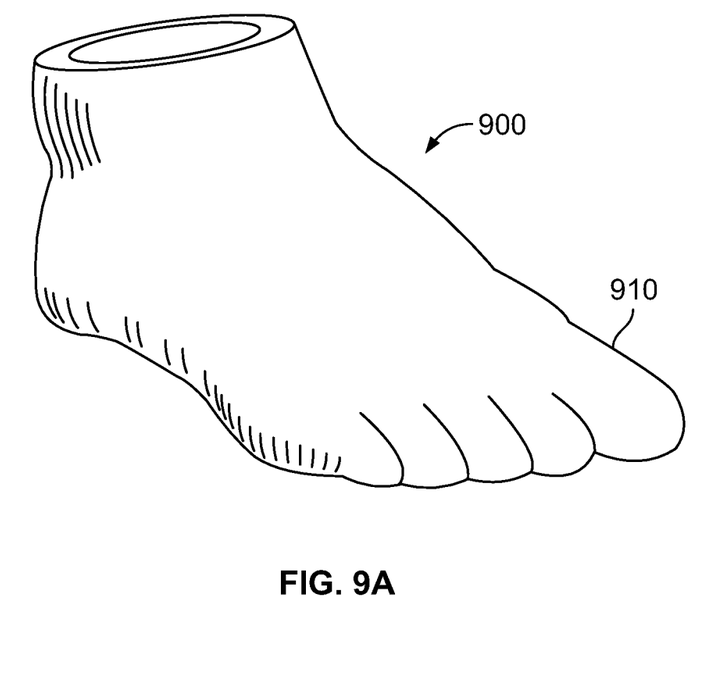
FIG. 9A depicts a side view of an artificial foot.
Figure 9B:
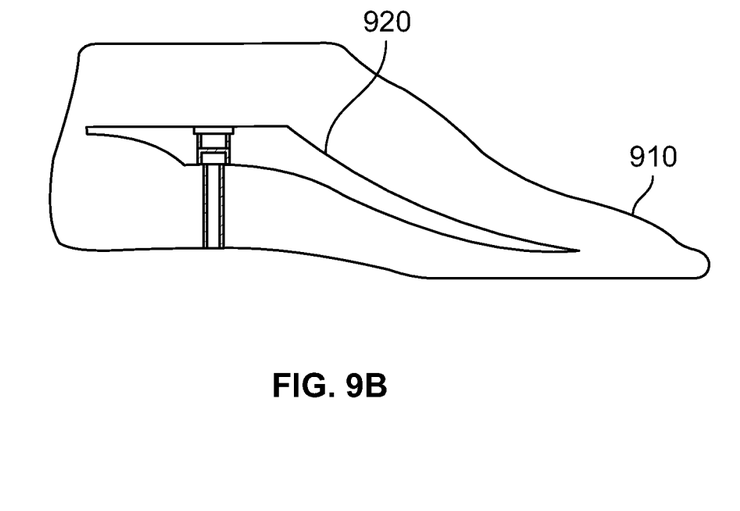
FIG. 9B depicts a side cutaway view of an artificial foot.

FIG. 9 depicts a conventional passive prosthetic foot 900, shown with foam footshell and inner keel 920. The keel 920 may be carbon-fiber or delrin and acts as a mechanical lever, providing support.

Currently, the mechanical characteristics of passive prosthetic ankles do not mirror those of the able-bodied ankle. This deficit is likely the cause of many challenges faced by below-knee amputees during locomotion. Such deficits include an 11-40% slower self-selected walking speed as well as a 10-60% greater metabolic cost of transport. Thus, a first step in improving the activity level, and quality of life, of below amputees is the development of biomimetic passive ankle prostheses.

The current design philosophy of passive prostheses limits their ability render biomimetic mechanical characteristics. The position dependent component of ankle torque—known as stiffness—defines the passive behavior of the prosthetic ankle during walking. Recently, the stiffness of the able-bodied ankle was compared to that of a standard passive prosthesis during the stance phase of walking (FIG. 8). Major differences arose in both the magnitude of the stiffness values and trends observed during the stance phase of walking. This is likely a result of the mechanical design of the passive ankle prostheses. Passive ankle prostheses often consist of a foam foot shell wrapped around a stiff plastic or carbon-fiber keel. The keel is a beam-like lever that is used to provide the reaction torque needed during walking, as well as store a limited amount of energy. However, as a result of the beam like design used in these devices, they are unable to increase their stiffness as stance phase progresses (i.e. hardening spring). Hence, passive prosthetic ankles are limited in their ability to provide biomimetic ankle stiffness properties and an opportunity exists to innovate on the design thereby positively impacting the lives of these amputees. Embodiments of the disclosed system may be simple, robust and lightweight.

What is claimed is:

1. An ankle prosthesis, comprising:
   a pneumatic piston disposed along an anterior-posterior axis of a foot of the ankle prosthesis;
   a spring disposed at an angle with respect to the pneumatic piston;
   wherein the pneumatic piston and spring are coupled together so as to store an energy produced by a dorsiflexion of the ankle prosthesis and release at least a portion of the stored energy during a plantarflexion of the ankle prosthesis.

2. The ankle prosthesis of claim 1, wherein the spring is a bending spring.

3. The ankle prosthesis of claim 2, wherein the bending spring is made of fiberglass.

4. The ankle prosthesis of claim 1, further comprising a mount for attachment of the ankle prosthesis to an artificial limb, wherein the spring is closer to the mount than the pneumatic piston.

5. The ankle prosthesis of claim 1, further comprising a valve coupled to the piston, the valve configured to open or close in order to permit or restrict the flow of gas between a first chamber and a second chamber of the pneumatic piston.

6. The ankle prosthesis of claim 5, wherein the valve is a solenoid valve.

7. The ankle prosthesis of claim 1, the ankle prosthesis having an increasing stiffness during use of the ankle prosthesis during a period of a stance phase of gait that comprises a push-off position.

8. The ankle prosthesis of claim 7, wherein the period of the stance phase of gait begins at a heel-strike position and ends at the push-off position.

9. An ankle prosthesis, comprising:
   a piston disposed along an anterior-posterior axis of a foot of the ankle prosthesis;
   a piston head disposed within the piston;
   a connecting rod coupled to the piston head and extending out from the piston;

a spring coupled to the connecting rod and disposed at an angle with respect to the piston, wherein the piston and spring store an energy produced by a dorsiflexion of the ankle prosthesis and release at least a portion of the stored energy during a plantarflexion of the ankle prosthesis.

\* \* \* \* \*